United States Patent
Darmos et al.

(12)

(10) Patent No.: US 10,548,661 B2
(45) Date of Patent: Feb. 4, 2020

(54) RADIOFREQUENCY PROBES WITH RETRACTABLE MULTI-TINED ELECTRODES

(71) Applicant: Diros Technology Inc., Markham (CA)

(72) Inventors: George Peter Darmos, Willowdale (CA); Ilya Gavrilov, Mississauga (CA); Peter George Darmos, Willowdale (CA)

(73) Assignee: Diros Technology Inc., Markham (CA)

(*) Notice: Subject to any disclaimer, the term of this patent is extended or adjusted under 35 U.S.C. 154(b) by 106 days.

(21) Appl. No.: 14/703,872

(22) Filed: May 4, 2015

(65) Prior Publication Data

US 2015/0313669 A1   Nov. 5, 2015

Related U.S. Application Data

(60) Provisional application No. 61/988,287, filed on May 4, 2014.

(51) Int. Cl.
```
A61B 18/14      (2006.01)
A61B 18/18      (2006.01)
A61B 18/00      (2006.01)
```
(52) U.S. Cl.
CPC .......... *A61B 18/148* (2013.01); *A61B 18/18* (2013.01); *A61B 2018/0091* (2013.01); *A61B 2018/00184* (2013.01); *A61B 2018/00214* (2013.01); *A61B 2018/00279* (2013.01)

(58) Field of Classification Search
CPC . A61B 18/08; A61B 18/082; A61B 2018/143; A61B 2018/00267
See application file for complete search history.

(56) References Cited

U.S. PATENT DOCUMENTS

| 5,551,426 | A | * | 9/1996 | Hummel | A61B 5/0422 600/374 |
| 5,893,847 | A | * | 4/1999 | Kordis | A61B 5/0422 600/374 |

(Continued)

OTHER PUBLICATIONS

Notification of Transmittal of the International Search Report and the Written Opinion of the International Searching Authority, or the Declaration, Dec. 21, 2015, Canadian Intellectual Property Office, PCT Application No. PCT/IB2015/001521, Inventor: George Peter Darmos, et al., Applicant Diros Technology Inc.

(Continued)

*Primary Examiner* — Ronald Hupczey, Jr.
(74) *Attorney, Agent, or Firm* — Everman Law Firm, P.A.; Gregory R. Everman

(57) ABSTRACT

A retractable, multi-tined radiofrequency (RF) probe operable for applying RF energy to tissue for therapeutic purposes, the probe having a tubular elongate member defining an interior and having a proximal end and an opposite distal end; a handle element at the proximal end of the elongate member; and an electrode element at the distal end of the elongate member, the electrode element comprising a tip portion and a plurality of tines, each of the plurality of tines being positionable in a retracted configuration within the interior of the tip portion and/or the elongate member and in a deployed configuration that extends outward of the tip portion.

20 Claims, 7 Drawing Sheets

(56) References Cited

U.S. PATENT DOCUMENTS

| | | | |
|---|---|---|---|
| 6,050,992 A * | 4/2000 | Nichols | A61B 18/1477 606/41 |
| 6,231,570 B1 * | 5/2001 | Tu | A61B 18/08 606/41 |
| 6,569,159 B1 * | 5/2003 | Edwards | C22F 1/183 606/41 |
| 6,652,516 B1 * | 11/2003 | Gough | A61B 18/1477 606/41 |
| 6,944,490 B1 * | 9/2005 | Chow | A61B 18/1492 600/374 |
| 7,229,438 B2 * | 6/2007 | Young | A61B 18/148 606/41 |
| 7,318,822 B2 | 1/2008 | Darmos et al. | |
| 8,337,492 B2 * | 12/2012 | Kunis | A61B 18/1815 606/41 |
| 2003/0045871 A1 | 3/2003 | Jain et al. | |
| 2004/0158239 A1 * | 8/2004 | Behl | A61B 18/1477 606/41 |
| 2004/0225286 A1 * | 11/2004 | Elliott | A61B 17/12036 606/41 |
| 2004/0254572 A1 * | 12/2004 | McIntyre | A61B 18/14 606/41 |
| 2006/0089635 A1 | 4/2006 | Young et al. | |
| 2006/0247620 A1 | 11/2006 | Bourne et al. | |
| 2007/0106292 A1 * | 5/2007 | Kaplan | A61B 18/1492 606/41 |
| 2012/0071712 A1 | 3/2012 | Manwaring et al. | |
| 2012/0310236 A1 | 12/2012 | Placek et al. | |

OTHER PUBLICATIONS

RS Medical, Multi-Tined Expandable Electrode for Radiofrequency Ablation, Jul. 2013.

* cited by examiner

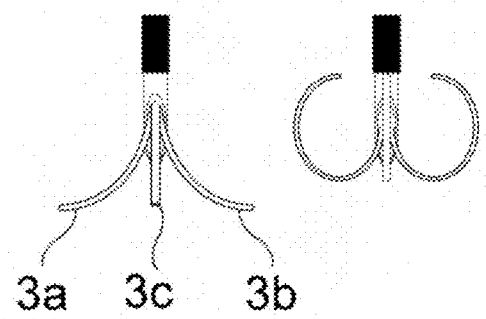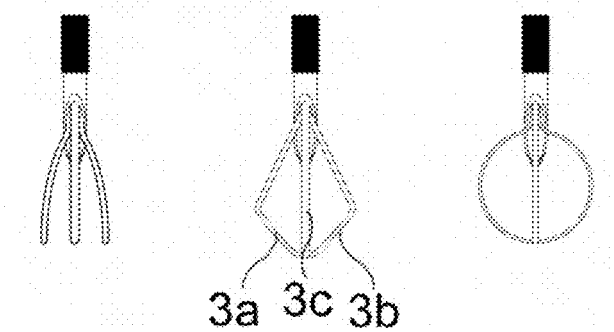
FIG. 2A  FIG. 2B  FIG. 2C  FIG. 2D  FIG. 2E
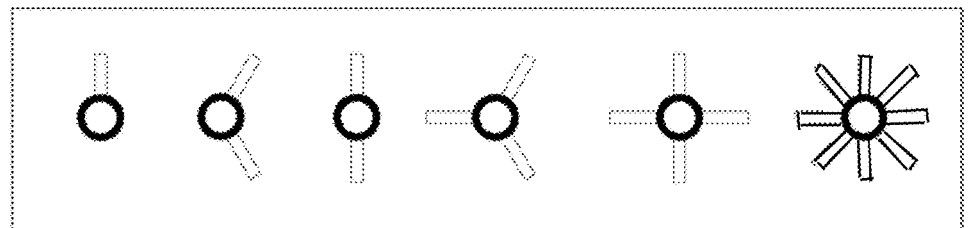
FIG. 2F
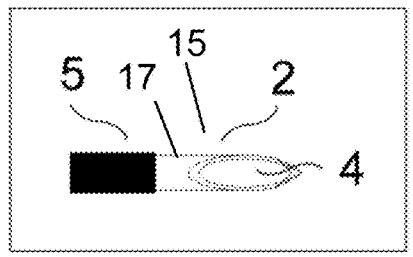
FIG. 2G

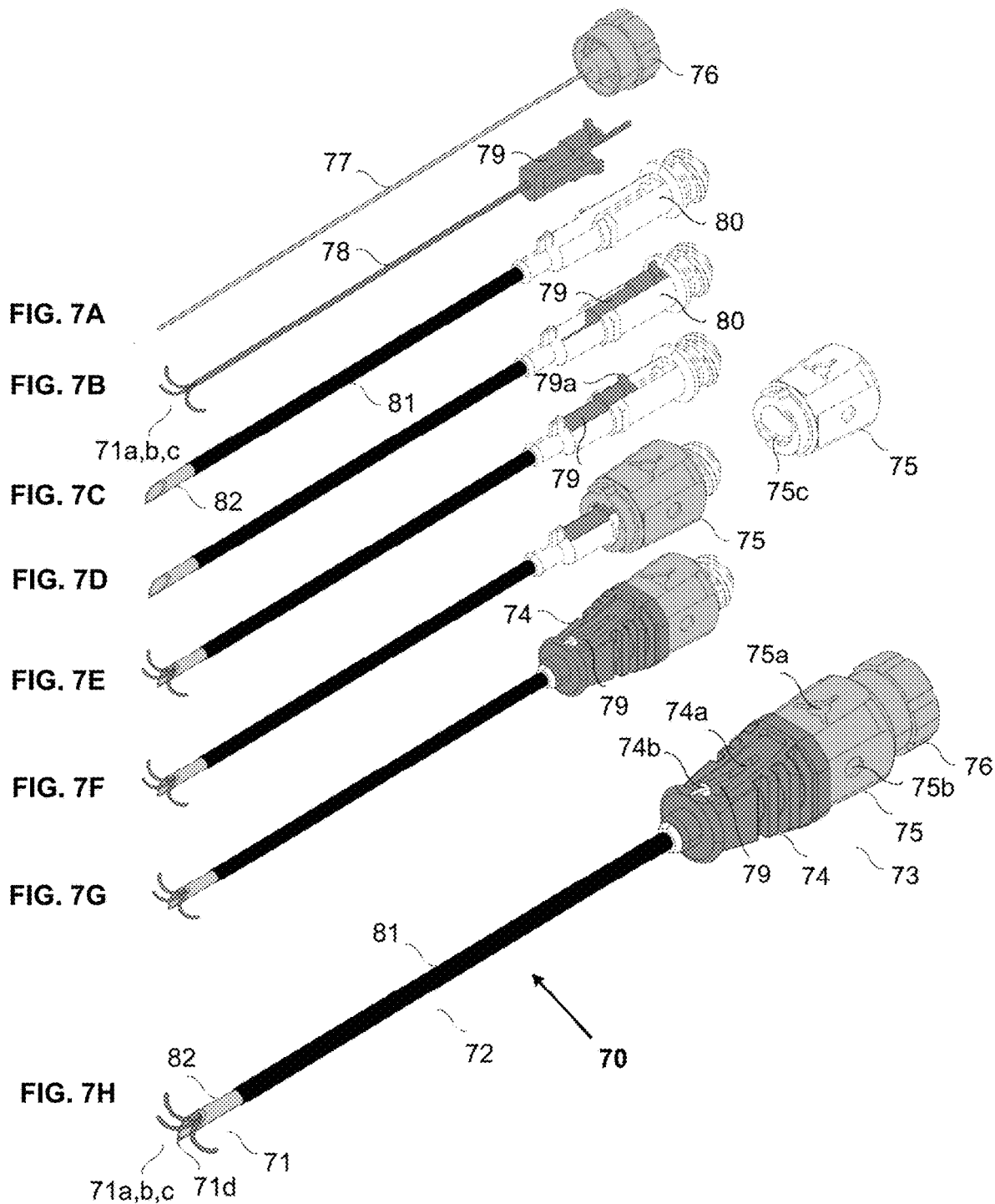

RADIOFREQUENCY PROBES WITH RETRACTABLE MULTI-TINED ELECTRODES

CROSS REFERENCE TO A RELATED APPLICATION

This application claims the benefit of U.S. Provisional Application No. 61/988,287, filed May 4, 2014, which is incorporated herein by reference in its entirety.

BACKGROUND OF THE INVENTION

Field of the Invention

The present invention relates to the field of radiofrequency (RF) ablation apparatuses and methods, and more specifically, to retractable, multipurpose, multi-tined RF cannulae and probes for the application of RF energy to tissue for therapeutic purposes.

Description of the Related Art

Radiofrequency (RF) energy can be applied for therapeutic pain management not relieved by conservative medical procedures by insertion of insulated cannulae with a bare metal tip into a target area of tissue such as neural structures centrally in a spinal space, paravertebral space, or an epidural space, or peripherally into spinal nerves or ganglia. Additional neural targets include intervertebral disc nerves within the disc nucleus or annulus fibrosis. RF energy can also be used for tumor ablation in structures such as the liver or bone. The RF energy can be applied in a continuous or pulsed manner. Both generally use sinusoidal waveforms at about 500 KHz, but the difference is that continuous RF applications are, as the name implies, continuous or uninterrupted, whereas pulsed RF consists of bursts or pulses of the same sinusoidal RF waveform separated by inactive or rest periods between pulses. A typical protocol for pulsed RF is two pulses per second, each lasting 20 milliseconds, with rest periods of 480 milliseconds between pulses.

Regardless of the RF modality—continuous or pulsed—a problem has been reliably and predictably conforming the ablation size, shape, and orientation to that of the tissue target, exactly for neural destructive procedures where unwanted extension may cause collateral damage to other, important neural structures, or purposely beyond the target in tumor destruction to create a margin of safety to include isolated regions of tumor extension. Too cautious an approach for neural destructive procedures to minimize the possibility of collateral nerve damage in pain management or the destruction of functional normal tissue in tumor ablation will, unfortunately, contribute to either less than optimal outcomes or procedure failures. Overcoming these deficiencies requires innovation in RF probe design that allows the deployment of multiple tined electrodes that can uniquely adapt their curvature and direction, and their extruded length, to generate RF lesions conforming to tissue target shape and orientation, and a size that best assures therapeutic efficacy and safely.

BRIEF SUMMARY OF THE INVENTION

To achieve the foregoing and other objects, the present invention, as embodied and broadly described herein, provides various embodiments of RF cannulae, probes, and electrode design that have been shown, in computer simulations and ex vivo experiments, to achieve the above stated innovations; thereby such innovations are predictive of improved therapeutic benefit in clinical applications.

In an embodiment, the present invention is a medical device for applying radiofrequency (RF) energy to tissue, including a tubular elongate member defining an interior and having a proximal end and an opposite distal end; a handle element at the proximal end of the elongate member; and an electrode element at the distal end of the elongate member, the electrode element comprising a tip portion and a plurality of tines, each of the plurality of tines being positionable in a retracted configuration within the interior of the tip portion and/or the elongate member and in a deployed configuration that extends outward of the tip portion. The medical device according to claim 1, wherein the tip portion has a distal opening therein, and wherein each of the plurality of tines is positionable in the deployed configuration through the distal opening. In an aspect of the present invention the tip portion has at least one side opening therein, and wherein at least one of the plurality of tines is positionable in the deployed configuration through the at least one side opening. In another aspect of the present invention, the plurality of tines define an arrangement in the deployed configuration that is operable for producing an ablation from the RF energy. In a further aspect of the present invention, the elongate member defines a longitudinal axis and wherein the electrode element has a plurality of slots with each slot extending generally parallel to the longitudinal axis, and wherein the plurality of tines is positionable in the deployed configuration through the plurality of slots. In still a further aspect of the present invention, each of the plurality of tines comprises a proximal portion disposed within the interior of the electrode element, an intermediate portion that extends laterally outward from the electrode element, and a terminal portion disposed within the interior of the electrode element. In yet another aspect of the present invention, each of the plurality of tines is made of an electrically conductive material. In another aspect of the present invention, electrode element is tubular, and wherein at least one of the plurality of tines extends laterally outward from the electrode element a distance that is greater than a diameter of the electrode element. In a further aspect of the present invention, each of the plurality of tines is made of a memory shape material, such as nickel/titanium alloy (Nitinol). In a further aspect of the present invention each of the plurality of tines comprises a distal end, and wherein the distal ends of the plurality of tines are joined together. In still another aspect of the present invention, the handle element comprises an actuator portion for positioning the plurality of tines at one of a plurality of positions between the retracted configuration and the deployed configuration. In an aspect of the present invention, the handle element further comprises a slider operably coupled to the actuator portion such that rotation of the actuator portion causes incremental movement of the slider to position the plurality of tines at the one of the plurality of positions between the retracted configuration and the deployed configuration. In still another aspect of the present invention, rotation of the actuator portion does not produce translational movement of the handle element or lengthening of the elongate member. In another aspect of the present invention, the electrode element comprises a first electrode element and a second electrode element, at least one of the first electrode element and the second electrode element comprising the plurality of tines. In an aspect of the present invention, the medical device includes a thermocouple probe having a proximal end disposed within the handle element and a distal end disposed within the electrode element. In another aspect of the present invention, the medical device includes an integrated fluid injector port disposed within the handle element.

In an embodiment, the present invention is a retractable, multi-tined radiofrequency (RF) probe operable for applying RF energy to tissue for therapeutic purposes, the probe including a tubular elongate member defining a generally hollow interior having a longitudinal axis, the elongate member having a proximal end and a distal end; a handle element disposed adjacent the proximal end of the elongate member; and a tubular electrode element disposed adjacent the distal end of the elongate member, the electrode element defining a generally hollow interior and a distal opening in communication with the generally hollow interior of the elongate member; wherein the handle element comprises an actuator portion operable for selectively positioning each of a plurality of tines between a retracted configuration and a deployed configuration; wherein the plurality of tines extend outward from the electrode element through the distal opening and are joined together.

In an embodiment, the present invention is a retractable, multi-tined radiofrequency (RF) probe operable for applying RF energy to tissue for therapeutic purposes, the probe including a tubular elongate member defining a generally hollow interior having a longitudinal axis, the elongate member having a proximal end and a distal end; a handle element disposed adjacent the proximal end of the elongate member; and a tubular electrode element disposed adjacent the distal end of the elongate member, the electrode element having a circular cross-section and defining a generally hollow interior and comprising at least one of a distal opening and a side opening in communication with the generally hollow interior of the elongate member; wherein the handle element comprises an actuator portion operable for selectively positioning each of a plurality of tines between a retracted configuration and a deployed configuration; and wherein the plurality of tines extend outward from the electrode element through the distal opening and/or through the side opening a lateral distance that is greater than a diameter of the electrode element. In an aspect of the present invention, at least one of the plurality of tines extends outward from the electrode element through the side opening and comprises a proximal portion that is disposed within the interior of the electrode element, an intermediate portion that is disposed outward of the electrode element, and a distal portion that is disposed within the interior of the electrode element.

BRIEF DESCRIPTION OF THE DRAWINGS

For a better understanding of the various embodiments described herein, and to show more clearly how these various embodiments may be carried into effect, reference will be made, by way of example, to the accompanying drawings. The skilled person in the art will understand that the drawings described below are for illustration purposes only and are not intended to limit the scope of the invention and its teachings in any way.

FIGS. 2A-G are fragmented views of the multi-tined RF probe of FIG. 1 wherein FIGS. 2A-E are top views showing exemplary configurations of multi-tined electrodes deployable through a distal opening in the tip portion of the electrode; and FIG. F shows distal end views of exemplary tine configurations of one, two, three, four and eight tines; and FIG. 2G shows the tip portion of the RF probe.

FIGS. 3A-G are fragmented views of a multi-tined RF probe according to the invention showing exemplary configurations of side exit deployable multi-tined electrodes wherein FIGS. 3A-E are top views of exemplary configurations of multi-tined electrodes deployable laterally through side slots of the electrode tip portion; FIG. F shows distal end views of exemplary tine configurations of one, two, three, four and eight tines; and FIG. 3G shows the tip portion of the RF probe.

FIGS. 7A-H show details of a handle assembly of a multi-tined RF probe according to an exemplary embodiment of the present invention.

Figures 1A, 1B, 1C, 1D, 1E:
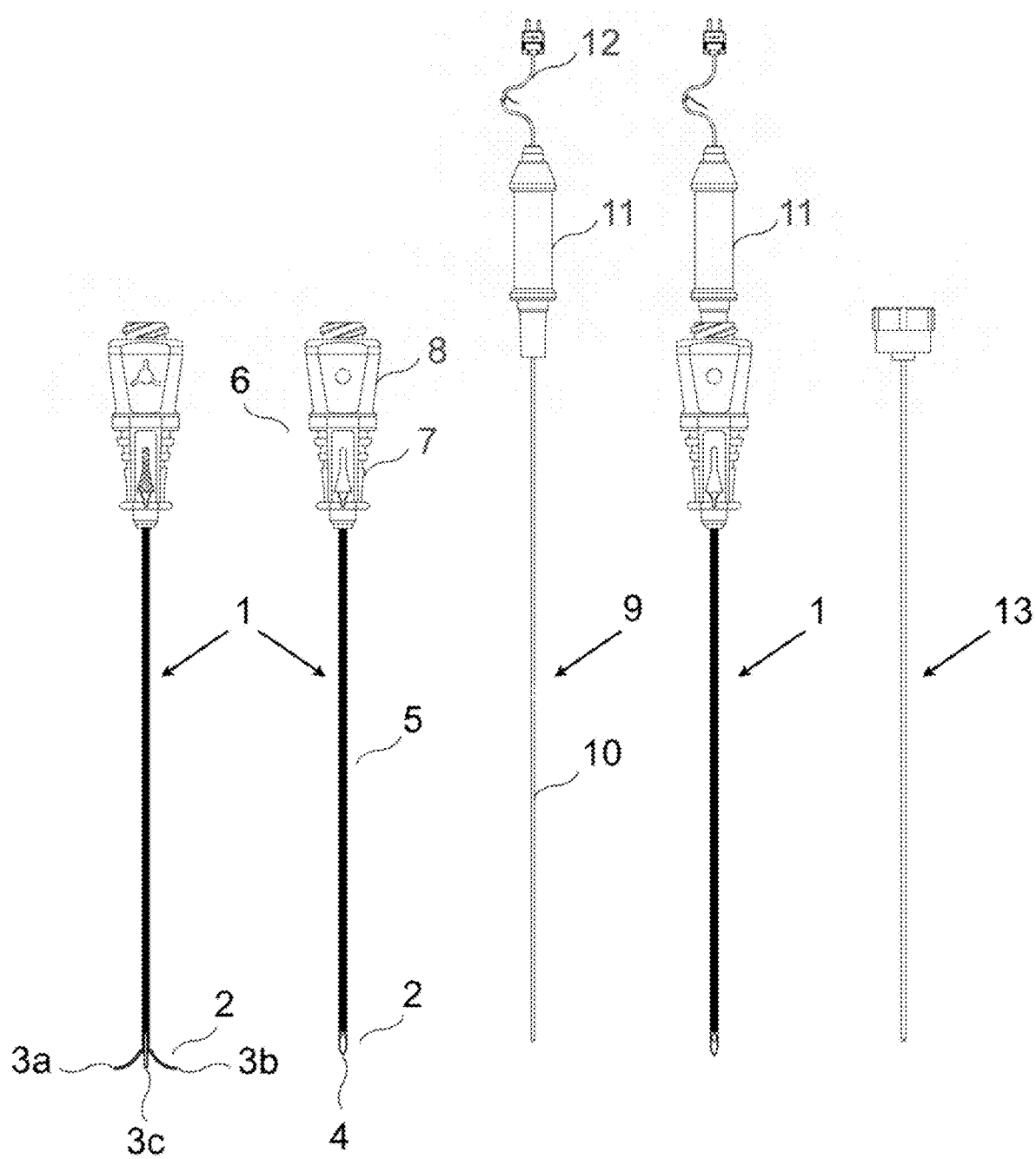
FIGS. 1A-E are top views of a multi-tined RF probe and its components according to an exemplary embodiment of the invention.

DESCRIPTION OF THE PREFERRED EMBODIMENTS various apparatuses and methods will be described hereinafter with reference to accompanying drawings to provide exemplary embodiments of the present invention. No embodiment described herein limits any invention and any invention may cover apparatuses or methods that differ from those described. The inventions are not limited to apparatuses or methods having all of the features of any one apparatus or method described below or to features common to multiple or all of the apparatuses or methods described below. Any invention disclosed in an apparatus or method described that is not claimed in this document may be the subject matter of another protective instrument, for example, a continuing patent application, and the applicants, inventors or owners do not intend to abandon, disclaim or dedicate to the public any such invention by its disclosure in this document. U.S. Pat. No. 7,318,822 B2, issued Jan. 15, 2008, is incorporated herein by reference in its entirety.

The terms "cannula," or "probe" used herein are meant to represent a medical device that comprises at least some of the functionality of each of a cannula or probe. It should also be noted that the term "handle" used herein is meant to represent an element that can be used as a means to hold a cannula or probe, control deployment of electrodes, and provide electrical connections, fluid injection ports, and the like. The term "distal" is used to generally indicate an element or portion of an element of a cannula or probe that is located closer to the working end of the cannula or probe. The term "proximal" is used to generally indicate an element or portion of an element that is located closer to the handle of the cannula or probe and further away from the working end of the cannula or probe. The term "working end" typically means the portion of the cannula or probe that is first inserted into a patient and is also the portion of the cannula or probe that provides various functions, such as at least one of fluid discharge, RF ablation, electrical stimulation, temperature sensing, and the like.

The various cannulae and probes described herein can also be used in other areas of a patient's body apart from neuronal or tumor tissue. Accordingly, the cannulae and probes to be described herein may make possible an enlarged range of applications at a greater number of locations than herein described, for example other types of excitable tissue such as skeletal and smooth muscle, or cells in general that rely on membrane electrical properties for their normal functionality. Furthermore, the various embodiments of the cannulae and probes described herein may be supplied, if so desired, as packaged, sterilized, single use, disposable products or alternatively as sterilizable, reusable products.

The following generalities apply to the various embodiment throughout this description:

(i) Material: Although stainless steel is a preferred metal used to fabricate RF cannulae and probes, other materials such as titanium, nickel/titanium alloys (Nitinol), as well as various other medical grade metals can be used as is known by those skilled in the art. In particular, Nitinol is a preferred memory metal for pre-shaped electrodes.

(ii) Cannula gauges: Monopolar probe arrangement (RF current is applied between an electrode on the working end of a probe and a large electrode on the skin): Typical range, 20 Ga-16 Ga; Range limits, 22 Ga-6 Ga.
Bipolar probe arrangement (RF current is applied between two electrodes on the working end of a probe): Typical range, 16 Ga-14 Ga; Range limits, 18 Ga-6 Ga.

(iii) Electrode length (distal length of tip portion plus furthest longitudinal reach of a tine): Typical range, 5 mm-10 mm; Range limits, 1 mm-25 mm.

(iv) Electrode tip portion outer diameter: Typical range 17 Ga (1.47 mm) to 20 Ga (0.91 mm).

(v) Tine lateral span (lateral distance between a tine and an elongate member longitudinal axis). Typical range, 0 mm to 4.0 mm; Range limits, 0 mm to 10 mm. Typical range for maximum lateral span, 2 mm to 6 mm, and more preferably 2 mm to 4 mm.

(vi) Shaft (tubular elongate member) length: Typical range, 5 cm-30 cm; Range limits, 2 cm-40 cm.

(vii) A probe or cannula distal end and/or the adjacent part of its elongate member can provide one or more exit points for fluid injection into tissue through one or more exit holes or slots as required, for example, for application of a local anesthetic or a corticosteroid.

(viii) Thermocouples are preferred for incorporation within probes for temperature sensing because of low cost, miniature size, and ease of fabrication, but other temperature sensing devices such as thermistors may be advantageously used.

The following sections will describe, initially, an example embodiment of a retractable multi-tined RF probe as used for therapeutic pain management and other RF procedures such as tumor ablation. This will be followed by other embodiments that further enhance the invention, or describe alternative apparatuses or methods for achieving similar or improved functionality.

FIGS. 1A-E illustrate an example embodiment of a multi-tined RF probe 1 that may be used for performing the RF ablation procedures described herein. In FIG. 1A three tines 3a, 3b, and 3c are shown deployed, and in FIG. 1B they are shown retracted. Multi-tined RF probe 1 comprises distally of an electrode element 2 and a tubular elongate member 5 which is connected to electrode element 2 distally and to a handle element 6 proximally. Electrode element 2 includes, in this example, three tines 3a-c and a tip portion 15 having a tubular portion 17 and a sharp, beveled tip 4 disposed distally thereof (see FIG. 2G). Elongate member 5, which is typically an insulated cannula, has one or more internal lumens. Handle element 6 comprises a hub portion 7 and an actuator portion 8. Hub portion 7 provides a means for gripping multi-tined RF probe 1 during a procedure, and actuator portion 8 provides a means for deploying, i.e. extruding tines 3a-c from the interior of elongate member 5 to beyond tip 4 and retracting, i.e. withdrawing them back into the interior of elongate member 5.

FIGS. 1C and 1E show other components that are used with multi-tined RF probe 1: a thermocouple probe 9 in FIG. 1C and stylet 13 in FIG. 1E. FIG. 1C shows thermocouple probe 9 comprising a tubular, uninsulated, elongate member 10 connected proximally to handle member 11. Tubular elongate member 10 has an interior lumen in which is positioned a thermocouple temperature sensor (not shown) at or near its distal end. The thermocouple is electrically connected to lead wire and plug 12. Elongate member 10 is also connected, independently, to lead wire and plug 12 thereby providing a conductive path for electrical stimuli or RF current to tip 2 of multi-tined RF probe 1 via contact of the exterior surface of elongate member 10 of thermocouple probe 9 to the interior surface of elongate member 5 of multi-tined RF probe 1.

Stylet 13 in FIG. 1E has a semispherical distal end which when fully inserted into the lumen of multi-tined RF probe 1 is positioned within the end of tip 2 to prevent tissue coring as multi-tined RF probe 1 is advanced toward a tissue target. FIG. 1D shows thermocouple probe 9 inserted into multi-tined RF probe 1 after a tissue target has been reached and stylet 13 removed.

RF Probes with Tip Exit Deployable Tines

An exemplary embodiment of the present invention is illustrated in FIGS. 2A to 2G. FIG. 2G shows a distal electrode element 2 of an RF probe, the electrode element 2 having a tip portion 15 with a tubular portion 17 and beveled tip 4. Also shown is a small segment of insulated elongate member 5. The tines are retracted into elongate member 5 and therefore cannot be seen. FIGS. 2A-E show exemplary configurations wherein three tines 3a, 3b, and 3c are deployed from tip 4 of an RF probe. The tines are constructed of electrically conductive materials such as stainless steel or nickel/titanium alloy (Nitinol). In these examples tines 3a, 3b, and 3c are electrically uninsulated, whereas in other examples part of some or all of the tines could be partially insulated. In order to obtain the example curvatures shown in FIGS. 2A-E, the shape memory property of Nitinol or spring steel can be used. These metals are preformed to take the shapes shown when not constrained, i.e. when deployed, but allow straightening in order to be retracted into elongate member 5. FIGS. 2A-C are examples of tines with their distal ends free, and FIGS. 2D-E are examples of tines with their distal ends joined together. Such constructions are used to achieve the exemplary configurations of FIGS. 2A-E: conical, butterfly, cup, octahedral, and spherical, respectively.

Further variations in ablation size, shape and orientation can be achieved by the use of tines of different diameters and/or lengths, and/or the number of tines contained in an RF probe, and/or selectively deploying at least one tine, and/or partially or fully deploying one or more tines. FIG. 2F shows, in distal end view, examples of RF probes containing one, two, three, four, or multiple tines. Tines can be positioned symmetrically about the probe longitudinal axis (and thusly elongate member 5 longitudinal axis) or alternatively may be asymmetrical if desired. The tines can be coplanor or skewed off plane, as illustrated in the second example of FIG. 2F. Skewed tines can be advantageous for certain applications where off-axis ablations are desirable. An additional feature of this invention is precise control of the extent of tine deployment, from partial to full, as will be described in a later section on the use of actuator portion 8 of handle element 6 shown in FIG. 1.

RF Probes with Side Exit Deployable Tines

Figures 3A, 3B, 3C, 3D, 3E:
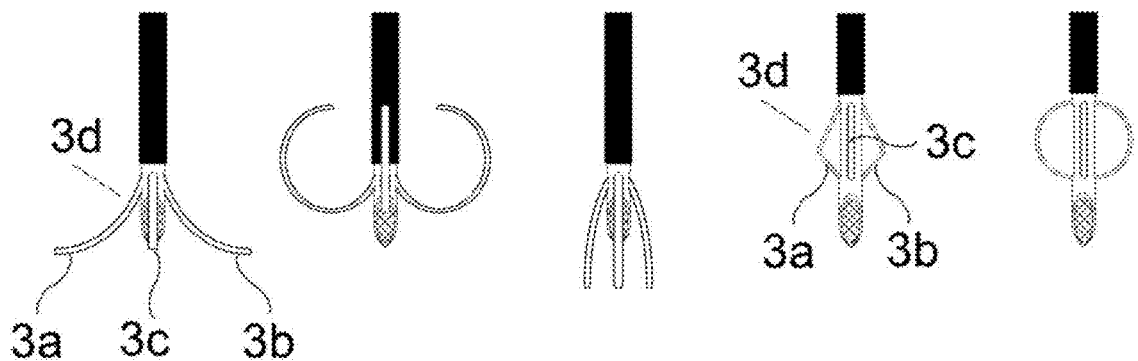
Figure 3F:
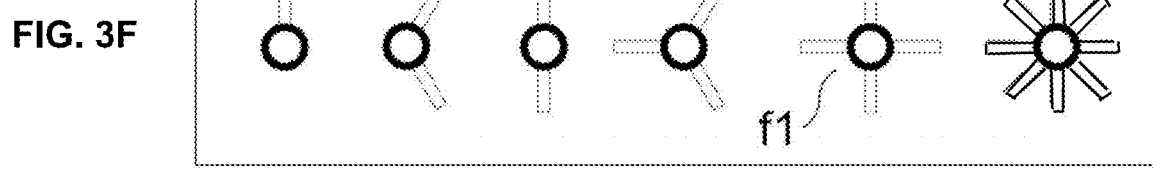
Figure 3G:
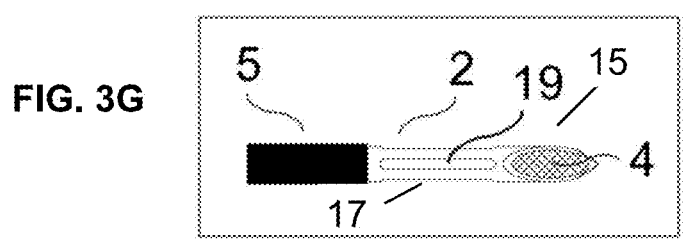

An exemplary embodiment of the present invention is illustrated in FIGS. 3A to 3G. FIG. 3G shows a distal electrode element 2 of an RF probe, the electrode element 2 having a tip portion 15 with a tubular portion 17 and beveled tip 4. Also shown is a small segment of insulated elongate member 5. The tines are retracted into elongate member 5. Unlike the embodiment of FIG. 2 in which the tines 3a-c deploy from an opening in tip 4, FIG. 3G reveals an elongated electrode element 2 that accommodates at least one side exit opening, preferably in the shape of a slot 19 having a longitudinal length parallel to the longitudinal axis of elongate member 5, through which tines are deployed. In this example there are four side exits slots 19, although only one can be fully seen. Tip 4 can be solid or patent, the latter to allow fluid exit from this point as well as from side exit slots. FIGS. 3A-E show example configurations in which four tines 3a-d are deployed from slots 19 of an RF probe. Tine 3d has a dashed connector line to indicate that in this view it cannot be seen exiting its slot. The tines are constructed of electrically conductive materials such as stainless steel or nickel/titanium alloy (Nitinol). In these examples tines 3a-d are electrically uninsulated, whereas in other examples part of some or all of the tines could be partially insulated. In order to assume the example curvatures shown in FIGS. 3A-E, the shape memory property of Nitinol or spring steel can be used. These metals are preformed to take the shapes shown when not constrained, i.e. when deployed, but allow straightening in order to be retracted into elongate member 5. FIGS. 3A-C are examples of tines with their distal ends free, and FIGS. 3D-E are examples of tines with their distal ends joined together. Such constructions are examples of how the different configurations of FIGS. 3A-E—conical, butterfly, cup, octahedral, and spherical, respectively, are obtained. It is further herein disclosed that tine configurations such as in FIGS. 3A, B, D, and E wherein tip 4 is the most distal point (or at least as distal) of electrode element 2 provide beneficial features of this invention. A first example: in radiofrequency neurotomies of lumbar medial branch nerves and sacral lateral branch nerves of posterior primary rami wherein it is desirable that tip 4 serves as a contact or anchor point on a periosteal surface in order to ensure that an RF ablation includes and extends from that surface in order to include target nerves in proximity to it. A second example: if electrode element 2 is constructed so that its tines exit some distance proximal to tip 4, as in FIGS. 3D and 3E and its surface is insulated distal to the tine exit point, then tip 4 can again serve as a tissue anchor point, but in this case to ensure that RF ablation will commence a distance proximal from tip 4 in order to, for example, preserve important regional structures. Such utility can be further enhanced by the addition of a radiopaque material to tip 4 so that it can be more easily visualized on radiography. Probe anchoring can be further augmented by imparting a corkscrew shape to tip 4 and rotating after tissue contact is made. Tip 4 can also be electrically isolated from the other portions of electrode element 2 thereby providing a means of impedance measurement as a guide for contact of tissue components of variable impedance such as bone, ligament, nerve, and fat.

Further variations in ablation size, shape and orientation can be achieved by the use of tines of different diameter and/or length, and/or the number of tines contained in an RF probe, and/or selectively deploying at least one of the tines, and/or partially or fully deploying one or more tines. FIG. 3F shows, in end view, examples of RF probes containing one, two, three, four, or multiple tines. For example FIGS. 3A-E use four equally spaced tines f1, as illustrated in the fifth example in FIG. 3F. Tines can be positioned symmetrically about the probe longitudinal axis, as shown in example f1, or alternatively may be asymmetrical if desired to achieve specific results. Furthermore, tines can be coplanor or skewed off plane, as illustrated in the second example in FIG. 3F. Skewed tines can be advantageous for certain applications where off-axis ablations are desirable. An additional feature of this invention is precise control of the extent of tine deployment, from partial to full, as will be described in a later section on the use of actuator 8 of handle 6 shown in FIG. 1.

Bipolar Multi-Tined RF Probes

Figure 4A:
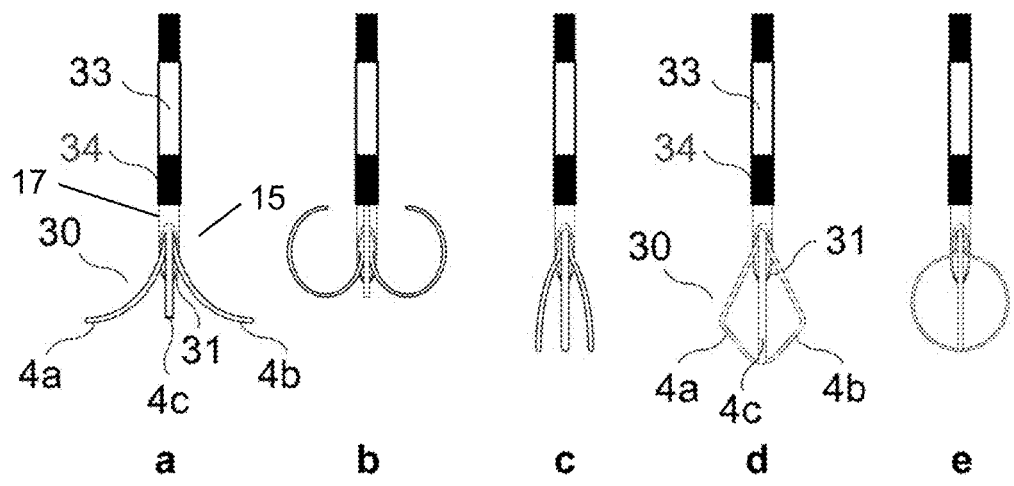
FIG. 4A, subparts a-e, are top views of bipolar, multi-tined electrodes deployable through a distal opening in a tip portion of a first electrode element according to exemplary embodiments of the invention.
Figure 4B:
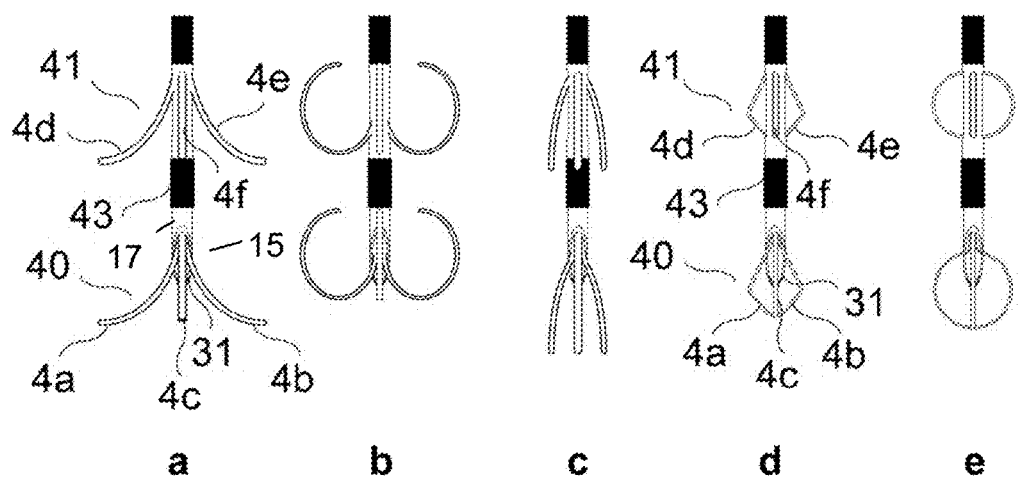
FIG. 4B, subparts a-e, are top views of bipolar, multi-tined electrodes deployable through a distal opening in a tip portion of a first electrode element and through side openings of a second electrode element according to exemplary embodiments of the invention.

An exemplary embodiment of the present invention is illustrated in FIGS. 4A and 4B which show drawings of various configurations of bipolar multi-tined RF probes. FIG. 4A shows examples a-e of a first electrode element 30 having at least one tine, for example a 3-tined first electrode element 30 of an RF probe with tip exit tines 4a, 4b, and 4c, and a tip portion 15 having a tubular portion 17 and a beveled tip 31. The tines are shown in their fully deployed state; otherwise they can be partially deployed or fully retracted, the latter as is necessary when advancing through tissue. A second electrode element 33, which in the examples of FIG. 4A are tubular shaped, is shown positioned more proximally, separated from first electrode element 30 by an insulated section 34. Electrode elements 30 and 33 comprise a bipolar configuration. It can be appreciated that the addition of other electrode elements similar to electrode element 33 may be advantageously used, creating tripolar, quadrapolar, etc. configurations. The electrode elements are constructed of electrically conductive materials such as stainless steel or nickel/titanium alloy (Nitinol).

Another example embodiment of this invention is illustrated in FIG. 4B which shows examples a-e of two 3-tined electrode elements 40 and 41 of an RF probe, first electrode element 40 comprising tip exit tines 4a, 4b, and 4c, and a tip portion 15 having a tubular portion 17 and a beveled tip 31; and second electrode element 41 having at least one tine, for example side exit tines 4d, 4e, and 4f deployed from slots. It is possible and may be advantageous in some applications for either or both electrode elements 40 and 41 to contain at least one tine. Electrode elements 40 and 41 are separated by an insulated section 43. The tines are shown in their fully deployed state; otherwise they can be partially deployed or fully retracted, the latter as is necessary when advancing through tissue. Multi-tined electrode elements 40 and 41 comprise a bipolar configuration. It can be appreciated that the addition of other side exit electrode elements may be beneficially used, creating tripolar, quadrapolar, etc. multitined electrode configurations.

In FIGS. 4A and 4B the tines 4a-c are constructed of electrically conductive materials such as stainless steel or nickel/titanium alloy. In the examples shown in FIGS. 4A and 4B, the tines are uninsulated, but in other examples part of some or all of them could be partially insulated. In order to assume the example curvatures shown in FIGS. 4A and 4B, the shape memory property of Nitinol or spring steel can be used. These metals are preformed to take the shapes shown when not constrained, i.e. when deployed, but allow straightening in order to be retracted. In FIGS. 4A and 4B there are examples of different tine configurations, a-e: conical, butterfly, cup, octahedral, and spherical, respectively.

Further variations in tine configuration and ablation size, shape and orientation can be achieved by the use of tines of different diameters and/or lengths, and/or the number of tines contained in the electrode elements of an RF probe, and/or selectively deploying a variable number of the tines available, and/or partially or fully deploying one or more tines. Furthermore, tines can exit from a distal opening of the tip portion 15 and/or slots proximal to the beveled tip 31 either symmetrically or asymmetrically spaced radially. Asymmetrical spacing allow tines to be skewed relative to a selected axial plane which can be advantageous for certain applications where off-axis ablations are desirable. In addition, a feature of this invention is the control of the extent of tine deployment, from partially to fully, and/or selective deployment of one or more multi tine elements, as will be described in a later section on the use of actuator portion 8 of handle portion 6 shown in FIG. 1.

Multi-Tined RF Probes with Integrated Temperature Sensor and Injection Port

Figures 5A, 5B:
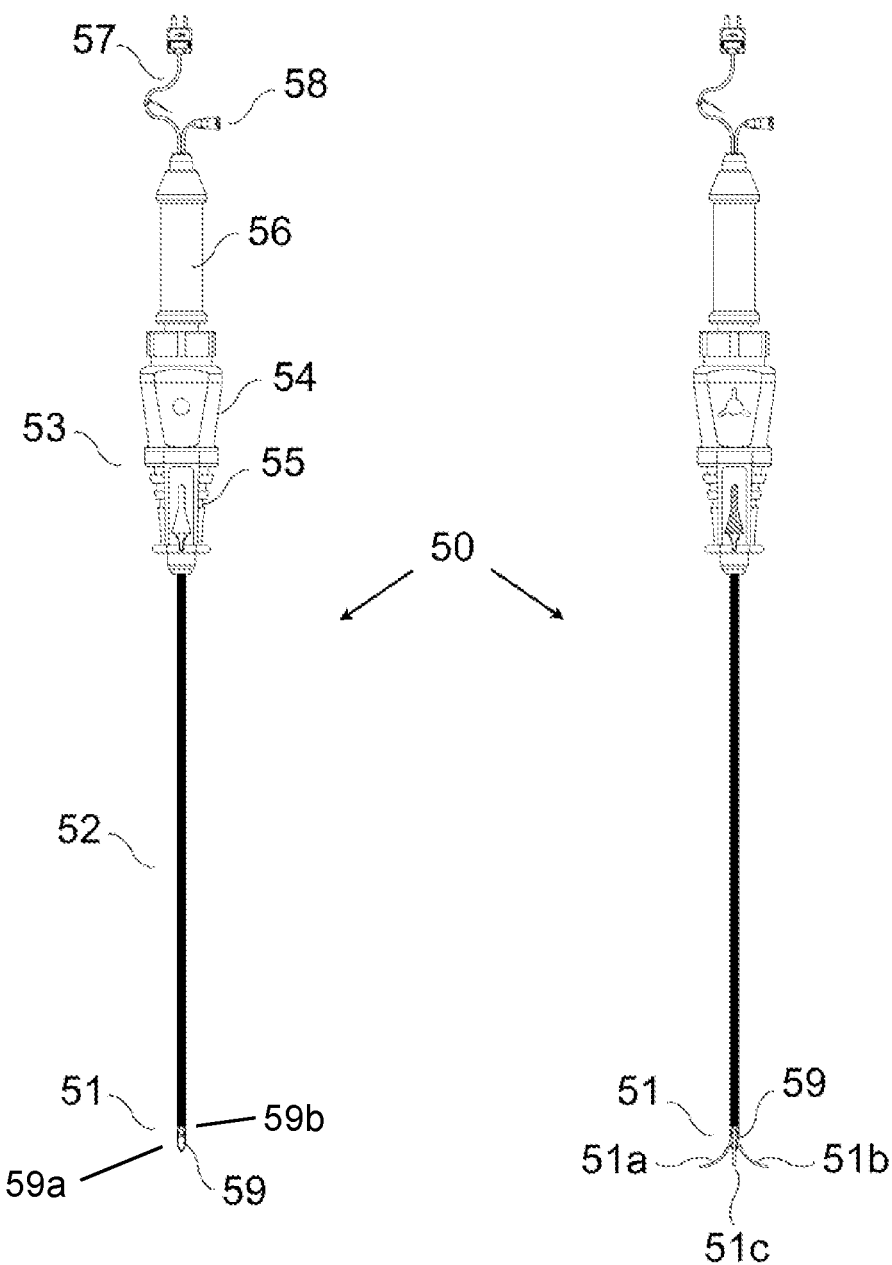
FIGS. 5A and B show an exemplary embodiment of a multi-tined RF probe with an integrated temperature sensor and injection port.

Another example embodiment of a multi-tined RF probe additionally comprises (1) an RF thermocouple probe that is permanently fixed within the multi-tined RF probe, and (2) an integrated fluid injection port, as will be illustrated in FIGS. 5 and 6. FIGS. 5A and 5B show multi-tined RF probe 50 comprised distally of electrode element 51 and a tubular elongate member 52 which is connected to electrode element 51 distally and to a handle element 53 proximally. Electrode element 51 includes, in this example, three tines 51a-c and a tip portion 59a having a tubular portion 59b and a sharp, beveled tip 59 disposed distally thereof. FIG. 5A illustrates tines that are fully retracted and therefore not visible, and FIG. 5B shows fully deployed tines. Elongate member 52, which typically has an insulated surface, has one or more internal lumens. Handle element 53 comprises a hub portion 55 and an actuator portion 54.

The proximal end of the handle of thermocouple probe 56 is fixed or fixed permanently in place within handle element 53 of multi-tined RF probe 50. Electrical connections are provided by cable and plug 57, and fluid instillation access is provided by injection port 58. Hub portion 55 provides a means for gripping multi-tined RF probe 50 during a procedure, and actuator portion 54 provides a means, generally by a rotational movement, for causing deployment of tines 51a-c from the interior of elongate member 52 to beyond tip 59 and, when desired, retracting the tines back into the interior of elongate member 52. It is to be noted that a feature of this embodiment is that an RF probe stylet is not needed and therefore the additional step of removing it prior to fluid injection is not required, avoiding possible movement or dislocation of the RF probe from stylet removal and then connection to a coupler for the injection.

Figure 6B:
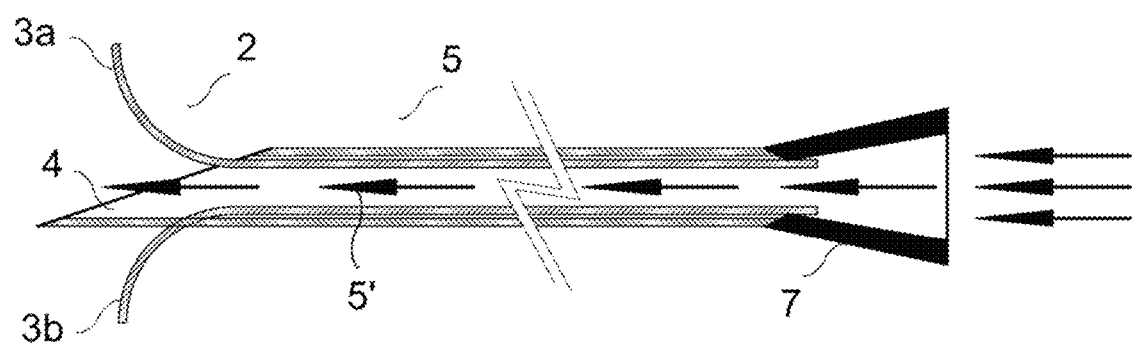
FIGS. 6A and B are sectional views showing the interior structure of the multi-tined RF probes of FIG. 1 and FIG. 5.
Figure 6A:
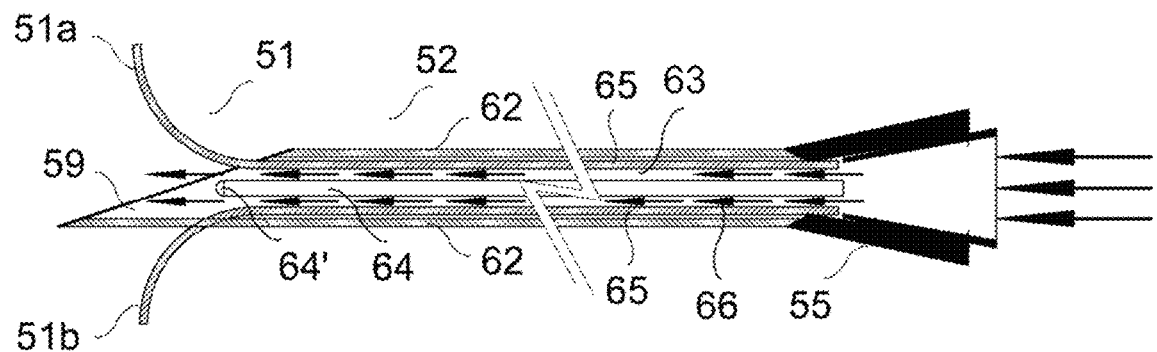

FIG. 6A is a sectional view of electrode element 51 and the adjacent section of elongate member 52 of multi-tined RF probe 50. This view shows a lumen 63 between the walls 62 of elongate member 52, said lumen being continuous distally with the interior of tip 59 and proximally with the interior space of hub portion 55. Within lumen 63 two tubular structures can be seen, thermocouple probe 64 and the walls of Nitinol tubing 65, whose tubular structure continues until its distal end at which point it has been severally split (splayed) in a longitudinal direction to form a cluster of electrodes, in this example curved tines 51a, 51b, and 51c (not shown). Thermocouple probe 64 is, in turn, enclosed within Nitinol tubing 65 and positioned so that its distal end, which contains thermocouple 64', is positioned at tip 59 in order to most accurately measure the temperature of an RF lesion. There is a channel 66, represented by arrows, between the outer wall of thermocouple probe 64 and the inner wall of Nitinol tubing 65 for fluid flow, providing means for a liquid instilled at injection port 58 (FIG. 5) to flow though fluid channel 66 and exit at tip 59.

For comparison, FIG. 6B shows a sectional view of electrode element 2 and the adjacent section of elongate member 5 of multi-tined RF probe 1 shown in FIG. 1. In this embodiment, thermocouple probe 9 is separate from multi-tined RF probe 1 and is typically inserted into it only when a target tissue has been reached and electrical stimulation for confirmation of the position of electrode element 2 or application of an RF lesion is required. When fluid instillation is required, thermocouple probe 9 must be removed in order to allow connection of injection tubing directly to handle element 6 of multi-tined RF probe 1. The channel for fluid flow represented by arrows 5' is shown.

Handle and Probe Assembly

Details of the construction of a multi-tined RF probe, such as the example embodiment of FIGS. 1A-E, is shown in FIGS. 7A-H. FIG. 7H shows a fully assembled multi-tined RF probe 70, comprising distally of an electrode element 71, a tubular elongate member 72 which is connected to electrode element 71 distally and to handle element 73 proximally. Elongate member 72 is typically a cannula that is covered by insulation 81 except at its distal end 82 where its surface is bare and tapers to beveled tip 71d. Electrode element 71 comprises tines 71a-c, cannula bare distal end 82, and beveled tip 71d. Handle element 73 comprises a hub portion 74 and an actuator portion 75. Hub portion 74 provides a means for gripping multi-tined RF probe 70 during a procedure, and actuator portion 75 provides a means for deploying tines 71a-c from the interior of elongate member 72 beyond tip 71d and retracting them back into the interior of elongate member 72.

FIG. 7A shows a stylet 77 with screw cap 76. Stylet 77 is inserted into multi-tined RF probe 70 and secured with a rotational motion. It is used when advancing through tissue to prevent coring of tissue into tip 71d. FIG. 7B shows Nitinol tubing 78 which is splayed at its distal end to form a cluster of tines 71a, b, and c, and a slider 79 which is fixed in place to Nitinol tubing 78. FIG. 7C shows insulated cannula 81 to which is attached at its proximal end handle substructure 80. The free end of handle substructure 80 is threaded to accept screw cap 76 of stylet 77. In the interior of handle substructure 80, and now disclosed as another feature of this invention, is a bored-out conical shaped element positioned longitudinally with its blunted apex distally and its base proximally. The material used for the conical shaped element is such that where the proximal end of tubing 78 penetrates the tight opening at the blunted conical apex, a leak-proof seal is formed to ensure that all injected fluid passes through the open proximal end of tubing 78 to exit its distal end at tip 71d and not elsewhere as can occur with other available devices. Errant fluid injection, especially of anesthetics, can cause confusion when assessing results of diagnostic anesthetic blocks and/or fail to mitigate pain during an RF lesion process. The leak-proof seal is maintained throughout the travel of slider 79.

FIG. 7D shows slider 79 added to substructure 80 (Nitinol tubing 78 is not visible). In this figure, slider 79 is at the most proximal extent of its range of motion, resulting in completely retracted tines. In FIG. 7E slider 79 is at the most distal extent of its range of motion, resulting in fully deployed tines. Also shown in FIG. 7E is tab 79a on the upper surface of slider 79. FIG. 7F shows actuator portion 75 added, with a stippled view revealing its inner threads 75c. Tab 79a of slider 79 engages inner threads 75c of actuator portion 75, establishing the mechanism wherein rotation of actuator portion 75, which in this example embodiment is 270°, moves slider 79 over its range of motion. The contiguous interior surface of actuator portion 75 and outer surface of substructure 80 contains a ball/detent system, or similar purpose mechanism, wherein the rotation of actuator portion 75 and therefore tine deployment can proceed in discrete, graded steps and additionally, if desired, be locked at any step.

FIG. 7G shows hub 74 added, with a small portion of slider 79 visible. FIG. 7H provides more detail on handle indicators 74a-b and 75a-b. Indicators 75a-b are engraved on the surface of actuator 75. When the 3-tine icon 75a in the up position (same as the direction of the open bevel of tip 71d) it indicates full tine deployment, as in FIG. 7H; when, after 270° rotation, the circular icon 75b is in the up position it indicates full tine retraction. Indicator 74a is a cutout on the top surface of hub 74 that allows the position of slider 79 to be seen. With tines retracted none of slider 79 is visible; during the process of tine deployment progressively more of slider 79 becomes visible until with full deployment all of cutout 74a is filled by slider 79. In this manner, the extent of tine deployment can be monitored. Tab indicator 74b is aligned with the direction of the open face of beveled tip 71d and thus is an indicator of the direction of tip 71d when it is in tissue and is no longer visible.

Another feature of this invention is that with tine deployment the rotation of the actuator portion 75 does not produce translational movement of the handle or the thermocouple probe. Only Nitinol tubing 78/slider 79 assembly has translational movement imparted to it, as is necessary to deploy or retract tines. In other devices currently available, their mechanism is such that rotation of the actuator portion 75 imparts translational movement to the handle and the thermocouple probe, as well as to the tines. As a result, rotation of actuator portion 75 to retract tines, required when advancing to a tissue target, produces lengthening of the RF probe because of its translational handle movement, causing the thermocouple probe to be pushed away from the RF probe tip. Therefore if opposite rotation of actuator portion 75 prior to the application of an RF lesion is less than is required for full deployment of tines, the thermocouple probe with the thermocouple at its tip, will remain proximal to the RF probe tip and probably beneath RF probe insulation, resulting in erroneous (too low) temperature readings and causing, as has occurred, an incorrect signal to the operator or RF generator automated temperature feedback to increase RF energy to dangerous levels.

Regardless of the foregoing detailed description of exemplary embodiments of the invention, the optimum dimensional relationships for the individual components of the invention, including variations in size, shape, thickness, form, materials, function and manner of operation, assembly and use, as well as equivalents thereof, are deemed to be readily apparent and understood by those skilled in the art. Accordingly, equivalent relationships to those shown in the accompanying drawing figures and described in the written description are intended to be encompassed by the invention, the foregoing being considered as illustrative only of the general concept and principles of the invention. Furthermore, since numerous modifications and changes will readily occur to those skilled in the art, the exemplary embodiments disclosed herein are not intended to limit the invention to the specific configuration, construction, materials and operation shown and described. Instead, all reasonably predictable and suitable equivalents and obvious modifications to the invention should be construed as falling within the scope of the invention as defined by the appended claims given their broadest reasonable interpretation in view of the accompanying written description and drawings.

That which is claimed is:

1. A medical device for applying radiofrequency (RF) energy to tissue, comprising:
   a tubular elongate member defining an interior and having a proximal end and an opposite distal end;
   a handle element at the proximal end of the elongate member; and
   an electrode element at the distal end of the elongate member, the electrode element comprising a tip portion and a plurality of tines, each of the plurality of tines being positionable in a retracted configuration within the interior of the tip portion and/or the elongate member and in a deployed configuration that extends outward of the tip portion;
   wherein the handle element comprises an actuator portion having an internal thread and a slider having a tab;
   wherein the tab extends only partially around a perimeter of the slider;
   wherein the internal thread engages the tab; and
   wherein rotation of the actuator portion causes the internal thread to impart translational movement to the tab and slider to position the plurality of tines at a position between the retracted configuration and the deployed configuration.

2. The medical device according to claim 1, wherein the tip portion has a distal opening therein, and wherein each of the plurality of tines is positionable in the deployed configuration through the distal opening.

3. The medical device according to claim 1, wherein the tip portion has at least one side opening therein, and wherein at least one of the plurality of tines is positionable in the deployed configuration through the at least one side opening.

4. The medical device according to claim 1, wherein the plurality of tines define an arrangement in the deployed configuration that is operable for producing an ablation from the RF energy.

5. The medical device according to claim 1, wherein the elongate member defines a longitudinal axis and wherein the electrode element has a plurality of slots with each slot extending generally parallel to the longitudinal axis, and wherein the plurality of tines is positionable in the deployed configuration through the plurality of slots.

6. The medical device according to claim 5, wherein each of the plurality of tines comprises a proximal portion disposed within the interior of the electrode element, an intermediate portion that extends laterally outward from the electrode element, and a terminal portion disposed within the interior of the electrode element.

7. The medical device according to claim 1, wherein each of the plurality of tines is made of an electrically conductive material.

8. The medical device according to claim 1, wherein the electrode element is tubular, and wherein at least one of the plurality of tines extends laterally outward from the electrode element a distance that is greater than a diameter of the electrode element.

9. The medical device according to claim 8, wherein each of the plurality of tines is made of a memory shape material.

10. The medical device according to claim 9, wherein the memory shape material is a nickel/titanium alloy.

11. The medical device according to claim 1, wherein each of the plurality of tines comprises a distal end, and wherein the distal ends of the plurality of tines are joined together.

12. The medical device according to claim 1, wherein rotation of the actuator portion does not produce translational movement of the handle element or lengthening of the elongate member.

13. The medical device according to claim 1, wherein the electrode element comprises a first electrode element and a second electrode element, at least one of the first electrode element and the second electrode element comprising the plurality of tines.

14. The medical device according to claim 1, further comprising a thermocouple probe having a proximal end disposed within the handle element and a distal end disposed within the electrode element.

15. The medical device according to claim 1, further comprising an integrated fluid injector port disposed within the handle element.

16. The medical device according to claim 1, wherein the plurality of tines are a splayed distal end portion of a conductive tube.

17. The medical device according to claim 1, wherein the handle element further includes an injection port and wherein in an internal channel extends from the injection port to the tip portion whereby fluid put into the injection port flows through the channel and exits the tip portion.

18. A retractable, multi-tined radiofrequency (RF) probe operable for applying RF energy to tissue for therapeutic purposes, the probe comprising:
   a tubular elongate member defining a generally hollow interior having a longitudinal axis, the elongate member having a proximal end and a distal end;
   a handle element disposed adjacent the proximal end of the elongate member; and
   a tubular electrode element disposed adjacent the distal end of the elongate member, the electrode element defining a generally hollow interior and a distal opening in communication with the generally hollow interior of the elongate member;
   wherein the handle element comprises an actuator portion operable for selectively positioning each of a plurality of tines between a retracted configuration and a deployed configuration;
   wherein the actuator portion has an internal thread and a slider having a tab;
   wherein the tab extends only partially around a perimeter of the slider;
   wherein the internal thread engages the tab;
   wherein rotation of the actuator portion causes the internal thread to impart translational movement to the tab and slider to position the plurality of tines at a position between the retracted configuration and the deployed configuration; and
   wherein the plurality of tines extend outward from the electrode element through the distal opening when in the deployed configuration and the tines are joined together.

19. A retractable, multi-tined radiofrequency (RF) probe operable for applying RF energy to tissue for therapeutic purposes, the probe comprising:
   a tubular elongate member defining a generally hollow interior having a longitudinal axis, the elongate member having a proximal end and a distal end;
   a handle element disposed adjacent the proximal end of the elongate member; and
   a tubular electrode element disposed adjacent the distal end of the elongate member, the electrode element having a circular cross-section and defining a generally hollow interior and comprising at least one of a distal opening and a side opening in communication with the generally hollow interior of the elongate member;
   wherein the handle element comprises an actuator portion having an internal thread and a slider having a tab;
   wherein the tab extends only partially around a perimeter of the slider;
   wherein the internal thread engages the tab;
   wherein rotation of the actuator portion causes the internal thread to impart translational movement to the tab and slider to retract or deploy the plurality of tines to position the plurality of tines at a position between the retracted configuration and the deployed configuration; and
   wherein the plurality of tines extend outward from the electrode element through the distal opening and/or through the side opening a lateral distance that is greater than a diameter of the electrode element when in the deployed configuration.

20. The probe according to claim 19, wherein at least one of the plurality of tines extends outward from the electrode element through the side opening and comprises a proximal portion that is disposed within the interior of the electrode element, an intermediate portion that is disposed outward of the electrode element, and a distal portion that is disposed within the interior of the electrode element.

* * * * *